United States Patent
Wessolowski et al.

[11] Patent Number: 5,369,945
[45] Date of Patent: Dec. 6, 1994

[54] METHOD AND APPARATUS FOR CONTROLLING THE YARN TENSION IN A FALSE TWIST TEXTURING MACHINE

[75] Inventors: Bernd Wessolowski, Remscheid; Bernd Neumann, Radevormwald; Hellmut Lorenz, Remscheid, all of Germany

[73] Assignee: Barmag AG, Remscheid, Germany

[21] Appl. No.: 15,462

[22] Filed: Feb. 9, 1993

[30] Foreign Application Priority Data

Feb. 10, 1992 [DE] Germany .............. 4203788

[51] Int. Cl.$^5$ .............. D01H 7/92; D02G 1/06
[52] U.S. Cl. .............. 57/264; 57/100; 57/332
[58] Field of Search ............... 57/100, 264, 280, 283, 57/332

[56] References Cited
U.S. PATENT DOCUMENTS

| | | | |
|---|---|---|---|
| 3,791,128 | 2/1974 | Landwehrkamp et al. | 57/100 |
| 3,842,578 | 10/1974 | Schippers | 57/280 |
| 4,015,414 | 4/1977 | Sholly | 57/264 |
| 4,248,038 | 2/1981 | Takai | 57/336 |
| 4,339,915 | 7/1982 | Dammann et al. | 57/339 |
| 4,720,702 | 1/1988 | Martens | 340/677 |
| 4,896,407 | 1/1990 | Haynes | 28/248 |
| 4,961,308 | 10/1990 | Braxmeier | 57/328 |
| 5,146,739 | 9/1992 | Lorenz | 57/264 |

FOREIGN PATENT DOCUMENTS

| | | |
|---|---|---|
| 2130550 | 9/1972 | Germany . |
| 3306594 | 11/1983 | Germany . |
| 4138509 | 8/1992 | Germany . |
| WO92/11535 | 7/1992 | WIPO . |

Primary Examiner—Daniel P. Stodola
Assistant Examiner—William Strysewski
Attorney, Agent, or Firm—Bell, Seltzer, Park & Gibson

[57] ABSTRACT

A method and apparatus for controlling a false twist texturing machine, which extends the previously known process for controlling operation during the normal operation of the machine, to exceptional operating conditions, such as during yarn thread-up and/or restarting after a temporary stoppage of operation by reason of a power failure. In accordance with the invention, the known method which includes control of the frictional force imparted to the yarn as a function of the yarn tension, is modified in such a manner that during periods other than normal operation, the control of the frictional force as a function of the yarn tension is terminated, and a predetermined frictional force is imparted to the yarn.

17 Claims, 2 Drawing Sheets

METHOD AND APPARATUS FOR CONTROLLING THE YARN TENSION IN A FALSE TWIST TEXTURING MACHINE

BACKGROUND OF THE INVENTION

The invention in general relates to a novel method of false twist texturing a yarn and, more particularly, to such a method providing for control of the tension imparted to the advancing yarn.

U.S. Pat. No. 5,146,739 to Lorenz discloses a yarn false twist texturing process and apparatus which includes monitoring the tension of an advancing yarn and processing the monitored tension signal to derive an adjusting signal which acts to control the false twisting unit in a manner providing a substantially constant tension. The process and apparatus disclosed in the Lorenz Patent are functioning satisfactorily in normal operations with the yarn having reached desired speed and temperature. However, the process and apparatus are not suited to funtion properly in non-normal operations as, for instance, during yarn thread-up operations, or when the machine decelerates because of temporary power failures or the like.

Except as otherwise noted herein, the yarn thread-up operation or procedure includes the steps of threading an advancing yarn into a first feed system, a heated plate, a cooling plate, and a false twist unit. It may also extend in the subsequent operating period in which the yarn has not yet reached its desired operating conditions.

Temporary electrical power failures occur relatively frequently; desirably, they should not, however, result in any broken yarns, since that would necessitate re-threading all of those yarns in the texturing machine. This would be particularly disconcerting in cases where such re-threading is carried out by automatic equipment, such as a doffer, movable along the front of the machine.

Accordingly, it is an object of the present invention to provide for a process and apparatus for controlling a false twist texturing machine by effectively controlling the operating parameters during periods of normal operation as well as during periods of other than normal operation, as, for instance, during yarn thread-up operations or during decelerations of the machine induced by temporary power failures.

It is more particular object of the present invention to provide for a process and apparatus of the kind referred to which better adapts the texturing machine to servicing by an automatic doffer.

SUMMARY OF THE INVENTION

The above and other objects and advantages of the invention are achieved in the embodiment illustrated herein by the provision of a process and apparatus which includes the steps of feeding an advancing yarn through a false twist unit which operates rotatably to impart a twisting component as well as a feeding component to the yarn, such components being a function of the frictional force applied by said unit to the yarn, monitoring the tension of the advancing yarn, and generating a signal (U) representative of the monitored tension. The generated tension signal (U) is processed through a time filter to produce a time averaged signal (MU) which, in turn, is compared with a fixed reference signal (Soll). Any difference in the signals thus compared yields an adjustment signal (VS). The false twist unit is controlled so that during periods of normal operation the frictional force imparted to the yarn varies is a function of the value of the adjusting signal (VS), and so that during periods during other than normal operations, a predetermined frictional force is imparted to the yarn which is not a function of the value of the adjusting signal (VS).

Moreover, the invention takes cognizance of frequently occurring power failures of short duration. While such power failures do not necessarily lead to yarn breakage, they may, because of defective twisting, lead to inferior yarn qualities. Such reductions in quality may be rooted in the design of the control circuit. The design should provide for sufficient stability, especially in close vicinity to the operation, to prevent excessive oscillations of the circuit without requiring, during a sudden power failure, elaborate adjustments in the control parameters. By way of the present invention such elaborate adjustments may be avoided.

In a preferred embodiment of the invention, the value of the frictional force imparted to the yarn during non-normal operating periods is greater than zero but less than the value of the frictional force applied during normal operations. In this manner, excessive tension on the yarn is avoided while, at the same time, continuing twisting results in greater strength of the yarn, which is particularly desirable during such periods of non-normal operation.

For reasons set forth below reduced tension peaks may be expected during the critical thread-up operation as a result of the continuing twisting action. Therefore, the method in accordance with the present application is of particular advantage in the thread-up of yarn at high running speeds. The reason for reduced tension peaks may be seen in the fact that twist increases as the applied frictional force is only gradually increased, whereas increasing the speed of the yarn to its operating speed takes place substantially immediately. Thus, in accordance with the present invention, a significant decrease in thread-up failures has been achieved.

During the thread-up steps referred to above, the predetermined frictional force may initially be set at a relatively low value and may subsequently be increased either gradually or intermittently. Advantageously, this provides for a gradual transition of the tension on the yarn between the yarn thread-up operation and the normal operating condition, so that possible tension peaks are likely to occur in small steps only.

The time of transition during and after yarn thread-up and during which the yarn tension control is non-operative, may be of predetermined duration after which the controlling step is operated in accordance with the periods of normal operation.

In another embodiment of the invention the yarn tension control for normal operation is actuated in dependence of measuring yarn tension and upon generation of an evaluation signal derived therefrom upon the tension reaching a predetermined desirable range. The tension level may be preset such that the actuation occurs at the earliest possible instant.

Advantageously, the actuation coincides with the termination of the gradual increase in the twisting action, i.e., as soon as the twisting has become stabilized.

The above cited patent to Lorenz further suggests that the quality of the yarn being produced in a false twist texturing process may be monitored by measuring the yarn tension. This feature may be incorporated in the present invention by including an evaluation signal which is derived from the monitored tension. More particularly, the continuous coefficient of variation (CV) derived from the continuously measured value of the monitored tension and the mean value continuously derived therefrom, may be determined and utilized as an evaluation signal. This is advantageous in that it permits determining fluctuations in yarn tension, which may be very small when the yarn is stationary, and to evaluate these fluctuations for purposes of commencing the yarn tension control under the normal operating conditions.

The evaluation signal may comprise a signal representing a standard deviation S derived from the square root of the mean square of the difference between the continuously measured value of the monitored tension and its mean value. In this way, absolute measuring results may be utilized in deriving the evaluation signal. Such absolute measuring results may be more representative, especially at large differences between measuring signal and mean signal, i.e. at high tension peaks, than the relative standard deviations.

During periods other than normal operations the predetermined frictional force may be determined on the basis of the reference signal from the yarn tension control circuit to take advanatge of the operational parameters of the control circuit which are preselected for optimum results in respect of such operational conditions as, for example, yarn speed, frictional force, feed components in the direction of yarn movement, twisting components acting transversely of the direction of movement, yarn quality, yarn strength, and twisting behavior.

In one preferred embodiment, the adjustment signal of the frictional force is selected as a function of those operating conditions extant during periods of other than normal operation. This is advantageous in that the given input of frictional force is adapted to the particular requirements of the yarn to be procecced.

The adjustment signal selected in the case of a power failure may thus be different from the signal utilized for yarn thread-up. This would apply in the majority of non-normal operating conditions encountered in practice.

The invention provides for different ways of adjusting the frictional force generated by the false twisting unit in normal as well as non-normal operation.

In a first embodiment means is provided for adjusting the frictional force as a function of yarn feed component relative to the twist component. These components, as used herein, are acting axially and transversely of the yarn, respectively.

In another embodiment means is provided for adjusting the frictional force by changes in the contact pressure the false twist unit exerts on the yarn.

In yet another embodiment means is provided for adjusting the rotational speed of the friction false twist unit to a value below its speed set for normal operations. This constitutes a particularly simple procedure for determining, temporarily storing, and recalling or resetting the speed of the friction false twist unit. Since the mathematical relationship between speed and friction force is always the same, the results of production, over a long time spans will be reproducible or predictable.

At a power failure the control circuit may be energized by a backup emergency power supply, and a predetermined value may be input as an adjustment signal which approximates the signal utilized in normal operations. Thus, control is provided in case of power failures, and undesirable oscillations of the control circuit, such as overshooting, are avoided.

The adjustment signal may be continuously read or determined and stored during normal operations, and upon a power failure, the value of the signal stored last may be used as the non-controlled adjustment signal. Thus, by way of particular advantage in cases of power failures of very short duration, it is the value of the signal obtained last during normal operation which controls the non-normal operation.

The predetermined adjustment signal for non-normal operations in all instances ranges from zero to the desired value of normal operation. Therefore, the transition or change-over from a non-normal to a normal operation is continuous and stable.

BRIEF DESCRIPTION OF THE DRAWINGS

Some of the objects and advantages of the present invention having been stated, others will appear as the description proceeds, when considered in conjunction with the accompanying schematic drawings, in which.

DETAILED DESCRIPTION OF THE PREFERRED EMBODIMENT

Figure 1:
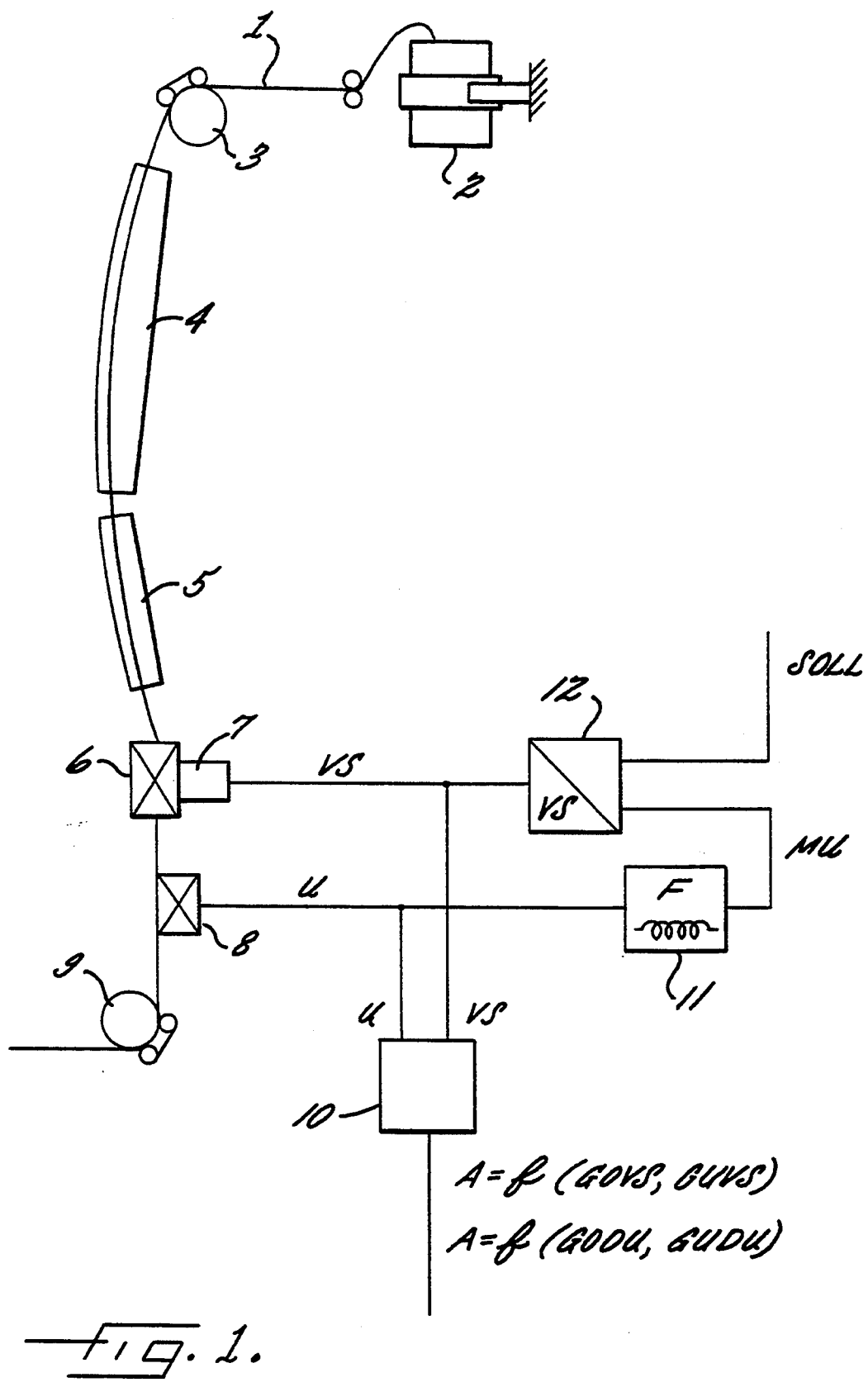
FIG. 1 is a schematic side elevation view of a yarn false twisting apparatus embodying the features of the present invention.

FIG. 1 is a schematic illustration of one of the yarn processing stations of a false twist texturing machine. A synthetic yarn 1 is unwound from a feed yarn package 2 by a feed system 3. A texturing zone is located intermediate the feed system 3 and a secpnd feed or delivery system 9, and comprises a heated plate 4, a cooling plate 5 and a friction false twist unit 6. The friction false twist unit 6 is provided with continuously movable surfaces which are moved transversely of the yarn axis and in contact therewith. These surfaces impart twist to the yarn which twist backs up in the direction of the feed system 3 and which twist is relaxed in the direction of delivery system 9. In addition to subjecting the yarn to a twist component the surfaces of the false twist unit 6 also impart to the yarn a feed component in the direction of yarn movement.

Between the friction false twist unit 6 and the delivery system 9 there is positioned a yarn tension measuring apparatus 8, which measures the yarn pulling force, hereinafter referred to as "yarn tension", which is converted to a signal U representative of the measured tension. It should be noted that while not shown, the yarn, downstream of the feed system 9, may be wound up and may be subjected to additional intermediate thermal processing.

The output signal U of the apparatus 8 is fed through a filter 11 to be converted a long-term time averaged signal MU. The time averaged signal MU is fed together with a reference value or signal (Soll) to a control 12. Signals MU and Soll are compared in the control 12 and any difference, after amplification, provides an adjustment signal VS. The adjustment signal VS is fed a member 7 which adjusts the twist imparted to the yarn by the friction false twist unit 6. Also, the feed component applied to the yarn by the false twist unit 6 is similarly controlled.

The output signal U of the tension measuring apparatus 8 and the adjustment signal are also fed to an evaluation unit 10 where the signal VS represents the mean tension value of the yarn. The output signal of the evaluation unit 10 is representative of the actually measured yarn tension, as described in U.S. Pat. No. 4,720,702. That is to say, within the evaluation unit 10 there stored an upper limit value GOVS and a lower limit value GUVS. Whenever the adjustment signal VS exceeds one of these limit values, an alarm signal A is actuated. Furthermore, after conversion of the actual yarn tension signal U and the adjustment signal VS to compatible formats, the evaluation unit 10 generates a signal DU representative of the difference therebetween. Finally, there are stored within the evaluation unit 10 upper limit value GODU and lower limit value GUDU of the difference signal DU. An alarm signal A is actuated, whenever the difference signal DU exceeds either of the limit values GODU, GUDU.

Advantageously, a standard deviation of yarn tension during a thread-up operation may be determined in the manner described in copending and commonly owned U.S. application Ser. No. 07/818,511. To this end, the yarn tension is measured and the measured value is converted, via a filter, to a mean value of the yarn tension. The measured value and its continuously formed mean value are subjected to subtraction, the difference signal is squared and thereafter filtered. The standard deviation S is derived by drawing the root of the filtered squared signal.

The adjustment apparatus 7 may, for example be a synchronous or asynchronous motor for rotatably driving the rotatable members of the friction false twist unit 6. Therefore, the difference between the time averaged signal and the reference signal is converted by unit 12 to a quantity, for example, a frequency, for controlling the speed of the drive motor 7 of the friction false twist unit 6.

Where the friction false twist unit 6 comprises three rotatable spindles mounted at the corners of an equilateral triangular bracket and supporting discs in a manner in which peripheral portions thereof are overlapping in the center of the triangular bracket, the adjustment device 7 may alternatively or additionally adjust the spacing between the spindles. For this purpose the spindles may be supported by rotatable eccentric mounting plates the relative disposition of which may be varied as a function of the adjustment signal VS, note DE-AS 21 30 550.

Where the friction false twist unit 6 comprises two disks between which the yarn may be clamped, one elastic disk being pressed against the other by a contact pressure device (note, for example, EP 22 743 A1, and U.S. Pat. No. 4,339,915), the contact pressure may be adjusted as a function of the adjustment signal VS, note DE 33 06 594 A1, and U.S. Pat. No. 5,146,739.

Where the friction false twist unit 6 comprises of two belts which rotate continuously and transversely of the yarn axis, and which frictionally engage the yarn between them, the belt mounting supports may be adjusted relative to each other by a predeterminable force (note, for example, U.S. Pat. No. 4,248,038), as a function of the adjustment signal VS.

Having regard to the different friction false twist units of the kind described by way of example, it should expressly be noted that the frictional force generated by them may be preset as a function of rotational speed since frictional force and speed are interrelated in friction false twist units.

To this end, the rotational speed may consitute the adjustment parameter either by itself or in concert with those measures described.

Figure 2:
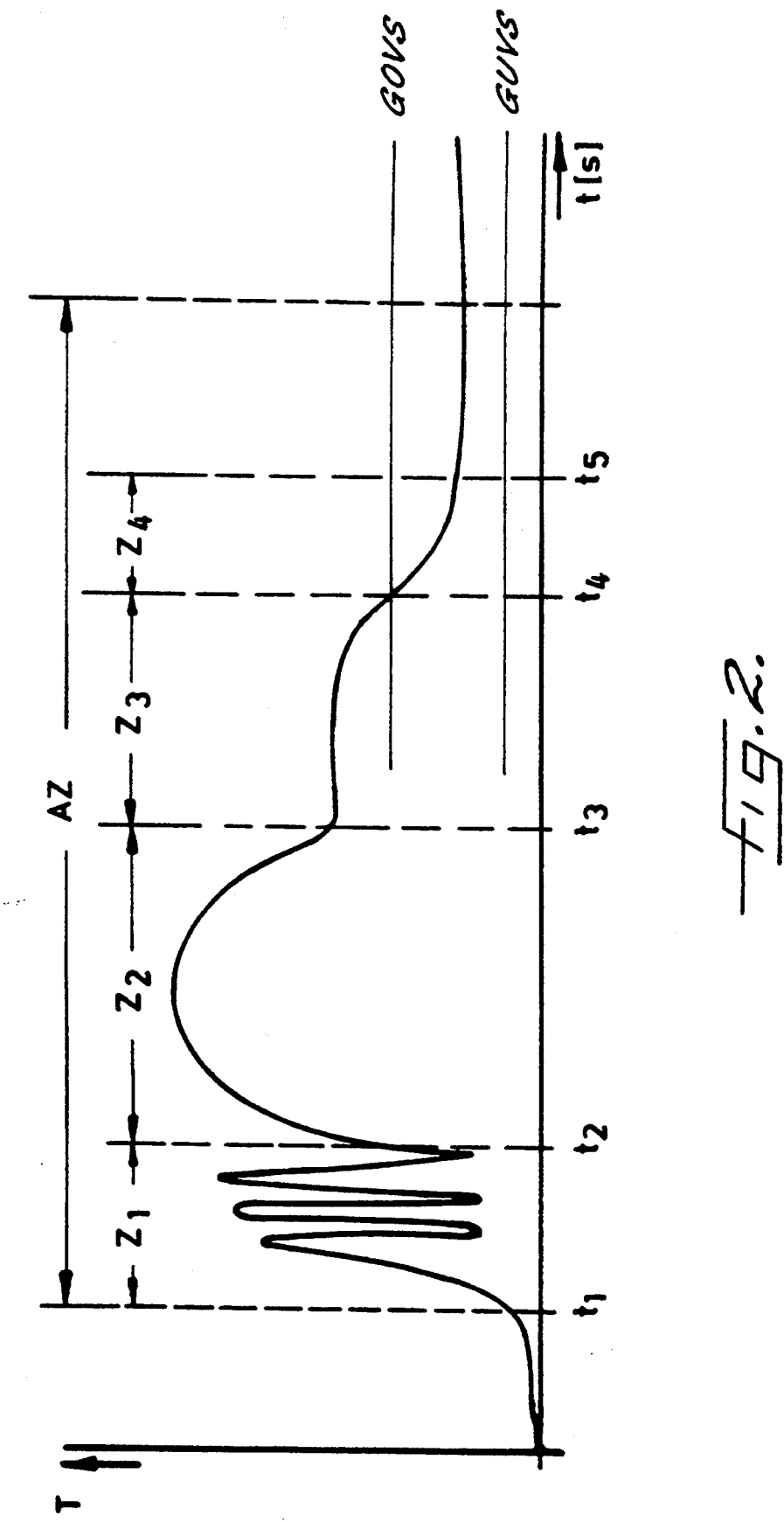
FIG. 2 is a diagram depicting yarn tension versus time during a thread-up operation, in accordance with the present invention.

Referring now to FIG. 2, the threading of a yarn will be described. As illustrated, the thread-up operation is divided into time zones Z1 to Z4. During time zone Z1, the yarn is withdrawn from supply package 2 by means of a suction gun (not shown) and inserted into delivery system 9, friction false twist unit 6, and yarn tension measuring apparatus 8. At this time the adjustment apparatus 7 of friction false twist unit 6 is not operating in its controlled mode, but is set at a constant value which is, for example, equal to or lower than the value desiable for normal operation.

Where the value is lower than that desirable value, there will be a build-up of low-density twist.

The yarn tension measuring apparatus 8 will respond even though the feed system 3 is not yet activated. However, movement of the yarn is very unstable at this point so that there are very large deviations in yarn tension as indicated by the CV value.

During thread-up time Z2, the yarn which continues to be withdrawn by the suction gun, is threaded onto heated plate 4 and cooling plate 5. Feed system 3 is engaged closed, so that the yarn is subjected to increased tension as a result of it being retained between feed systems 3 and 9 and their different speeds, as well as the increasing twist buildup. As a result, movement of the yarn becomes more stable and the standard deviations are reduced.

During thread-up time Z3, movement of the yarn has become stable. The standard deviation falls below a predetermined limit value. The thread-up time Z3 is therefore a testing time. During this testing time, it is determined whether the limit value of the standard deviation is excessive. When the standard deviation does not exceed the limit value during the testing time, the yarn tension control will be actuated upon expiration of the testing time, in that the yarn tension 8 and the adjustment apparatus 7 of friction false twist unit 6 to be predetermined are included in a control circuit. The adjustment device which allows the frictional force of friction false twist unit 6 to be predetermined is adjusted such that yarn tension measuring apparatus 8 indicates a substantially constant yarn tension.

Should breakdowns continue to occur during the testing time, the testing time Z3 will be restarted after it has expired.

Upon successful completion of the testing time for the standard deviation, the yarn tension control operates with a predetermined desired value of the yarn tension. During thread-up time Z4, the adjustment device 7 adjusts itself such that the yarn tension reaches its desired value.

After expiration of the above described testing time Z3, monitoring of the quality is commenced. Yarn tension is now being monitored in the manner aforesaid. What is monitored is whether the yarn tension, or evaluation signals derived therefrom, and/or the adjustment signal fed to adjustment device 7 leave predetermined tolerance ranges. These results may be registered alone or in concert, so as to determine the quality of the produced package.

For example, when the machine is improperly adjusted or when machine parts are defective, it is possible that during the testing time Z3 the predetermined desired value of the yarn tension and/or the desired value of the adjustment force are not reached. In such a case, quality control is commenced in any event after expiration of a total thread-up time, which is greater than the sum of the aforesaid times Z1–Z4, thereby ensuring that in the event of an incorrect machine setting or malfunctions of the machine, quality defects of the package can be recognized and eliminated.

The measures provided by the present invention permit an immediate response in the event of quality deviations as a result of non-normal operating conditions, so as to achieve the desired quality. Otherwise, there is always the possibility of cutting the yarn, should it not be possible to control quality defects.

In the drawings and specification, there has been set forth a preferred embodiment of the invention, and although specific terms are employed, they are used in a generic and descriptive sense only and not for purposes of limitation.

That which is claimed is:

1. A yarn false twist texturing process having provision for controlling the tension imparted to an advancing yarn, comprising the steps of
    feeding the advancing yarn at a desired speed through a false twist unit which acts to impart a frictional force to the yarn which has a twisting component and a tension imparting component, and so as to define periods of normal operation for the advancing yarn,
    monitoring the tension of the advancing yarn and generating a signal (U) representative of the monitored tension,
    processing the generated tension signal (U) through a time filter to produce a time averaged signal (MU),
    comparing the time averaged signal (MU) with a set point signal (Soll) and producing an adjusting signal (VS) representing the difference therebetween, and
    controlling the operation of the false twist unit so that during said periods of normal operation, the frictional force imparted to the advancing yarn varies as a function of the value of the adjusting signal (VS), and so that during periods other than said periods of normal operation, a predetermined frictional force is imparted to the advancing yarn which is not a function of the value of the adjusting signal (VS).

2. The process as defined in claim 1 wherein said predetermined frictional force has a value greater than zero but less than the value of the frictional force imparted during said periods of normal operation.

3. The process as defined in claim 1 wherein said periods other than said periods of normal operation include the initial steps of threading the advancing yarn through a first feed system, a heated plate, a cooling plate, and said false twist unit, and during said initial steps said predetermined frictional force is initially set at a low value and then increased.

4. The process as defined in claim 1 wherein said periods other than said periods of normal operation include the initial steps of threading the advancing yarn through a first feed system, a heated plate, a cooling plate, and said false twist unit, and wherein said periods other than said periods of normal operation have a predetermined duration, after which said controlling step is operated in accordance with said periods of normal operation.

5. The process as defined in claim 1 wherein said controlling step includes shifting from operation in accordance with said periods other than said periods of normal operation to operation in accordance with said periods of normal operation upon the monitored tension reaching a predetermined level and upon evaluation of a separate evaluation signal which is derived from the monitored tension signal.

6. The process as defined in claim 5 wherein said evaluation signal comprises the continuous coefficient of variation (CV) and which is derived from the continuously measured value of the monitored tension and the mean value continuously derived therefrom.

7. The process as defined in claim 5 wherein said evaluation signal comprises the standard deviation S which is obtained from the square root of the squared difference between the continuously measured value of the monitored tension and its mean value.

8. The process as defined in claim 1 comprising the further step of monitoring the quality of the advancing yarn which includes the evaluation of an evaluation signal which is derived from the monitored tension.

9. The process as defined in claim 1 wherein during said periods other than said periods of normal operation the predetermined frictional force is determined by an adjustment signal.

10. The process as defined in claim 9 wherein said adjustment signal is predetermined so as to impart a predetermined twisting component and a predetermined tension component to the advancing yarn.

11. The process as defined in claim 9 wherein said adjustment signal is predetermined as to impart a predetermined contact pressure between said false twist unit and the advancing yarn.

12. The process as defined in claim 9 wherein said adjustment signal is predetermined so as to impart a predetermined speed to the advancing yarn which is below said desired speed during said periods of normal operation.

13. The process as defined in claim 9 wherein a value for said adjustment signal is periodically stored during said periods of normal operation, and upon a general power failure the last stored value is utilized to determine the predetermined frictional force.

14. An apparatus for false twisting texturing an advancing yarn comprising
    yarn false twisting means for imparting a frictional force to an advancing yarn which has a twisting component and a tension imparting component,
    sensor means positioned downstream of said yarn false twisting means for continuously monitoring the tension of the advancing yarn and generating a signal (U) representative of the tension,
    circuit means operatively connected to said sensor means for continuously determining a time averaged value (MU) of the monitored tension signal (U), for also continuously comparing the time averaged value (MU) and a set point value (Soll) and producing an adjusting signal (VS) representing the difference between the time averaged value (MU) and the set point signal (Soll), and
    control means for controlling the operation of the false twisting means so that during periods of normal operation wherein the yarn is advanced at a desired speed, the frictional force imparted to the advancing yarn varies as a function of the value of the adjusting signal (VS), and so that during periods other than said periods of normal operation, a predetermined frictional force is imparted to the advancing yarn which is not a function of the value of the adjusting signal (VS).

15. The apparatus as defined in claim 14 wherein said control means includes a control circuit for delivering an adjustment signal to said yarn false twisting means during said periods other than said periods of normal operation and so that said yarn false twisting means imparts said predetermined frictional force to the yarn.

16. The apparatus as defined in claim 15 wherein said control means further includes an emergency power source for powering said control circuit upon a general power failure.

17. The apparatus as defined in claim 14 wherein said circuit means includes means for comparing the adjusting signal (VS) with the tension signal (U) and producing a differential signal (DU) representing the difference therebetween, and further comprising means for generating an alarm whenever at least one of the following conditions is present: (1) the adjusting signal (VS) leaves a predetermined range, and (2) the differential signal (DU) leaves a second predetermined range.

* * * * *